US012589135B2

(12) United States Patent (10) Patent No.: US 12,589,135 B2

Banov et al. (45) Date of Patent: Mar. 31, 2026

(54) TOPICAL ADMINISTRATION OF GLP-1 RECEPTOR AGONISTS

(71) Applicant: CMPD Licensing, LLC, Conroe, TX (US)

(72) Inventors: Daniel Banov, Sugar Land, TX (US); Gus Bassani, Houston, TX (US); Jay Richard Ray, II, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 0 days.

(21) Appl. No.: 18/236,300

(22) Filed: Aug. 21, 2023

(65) Prior Publication Data

US 2025/0064897 A1 Feb. 27, 2025

(51) Int. Cl.
| | |
|---|---|
| *A61K 38/26* | (2006.01) |
| *A61K 9/00* | (2006.01) |
| *A61K 47/14* | (2017.01) |
| *A61K 47/18* | (2017.01) |
| *A61K 47/24* | (2006.01) |
| *A61K 47/26* | (2006.01) |
| *A61K 47/32* | (2006.01) |
| *A61K 47/38* | (2006.01) |

(52) U.S. Cl.
CPC .............. *A61K 38/26* (2013.01); *A61K 9/006* (2013.01); *A61K 47/14* (2013.01); *A61K 47/18* (2013.01); *A61K 47/24* (2013.01); *A61K 47/26* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 4,935,428 | A | 6/1990 | Lewis | |
| 11,503,848 | B2 * | 11/2022 | D'Hoore ................... | A23L 2/60 |
| 11,571,385 | B2 | 2/2023 | Amano | |
| 2003/0219472 | A1 | 11/2003 | Pauletti | |
| 2006/0127473 | A1 | 6/2006 | Nichols | |
| 2007/0059254 | A1 | 3/2007 | Singh | |
| 2007/0104741 | A1 | 5/2007 | Murty | |
| 2007/0166336 | A1 | 7/2007 | Delmarre | |
| 2009/0118211 | A1 | 5/2009 | Drai | |
| 2009/0186896 | A1 | 7/2009 | Ulbric | |
| 2010/0159007 | A1 | 6/2010 | Staniforth | |

| | | | | |
|---|---|---|---|---|
| 2013/0303495 | A1 | 11/2013 | Dhingra | |
| 2015/0005307 | A1 | 1/2015 | Sams | |
| 2019/0275006 | A1 | 9/2019 | Hsu | |
| 2019/0275060 | A1 | 9/2019 | Giliyar et al. | |
| 2021/0087250 | A1 * | 3/2021 | Werle ................... | A61K 47/183 |
| 2021/0260077 | A1 * | 8/2021 | Liolios ................... | A61K 47/14 |
| 2025/0114370 | A1 | 4/2025 | Pergolizzi | |

FOREIGN PATENT DOCUMENTS

| | | | | |
|---|---|---|---|---|
| CN | 104055735 | A * | 9/2014 | |
| WO | WO-2017093810 | A2 * | 6/2017 | ............. A61K 38/19 |
| WO | 2025104674 | | 5/2025 | |

OTHER PUBLICATIONS

Guo et al. "Emerging strategies for enhancing buccal and sublingual administration of nutraceuticals and pharmaceuticals" Journal of Drug Delivery Science and Technology, 2019, 52, 440-451. (Year: 2019).*

Rahman et al. "Role of excipients in successful development of self-emulsifying/microemulsifying drug delivery system (SEDDS/SMEDDS)" Drug Development and Industrial Pharmacy, 2013, 39, 1-19 (Year: 2013).*

Rybelsus semaglutide tablets, Prescribing Information, Novo Nordisk A/S, Denmark, 2017.

Wegovy—semaglutide injection, solution, Prescribing Information, Novo Nordisk A/S, Denmark, 2017.

Ozempic—semaglutide injection, solution, Prescribing Information, Novo Nordisk A/S, Denmark, 2017.

Mounjaro—tirzepatide injection, solution, Prescribing Information, Eli Lilly and Company, 2022.

International Search Report and Written Opinion, PCT/US2024/043208, Dec. 11, 2024.

Haddadzadegan et al., Oral delivery of therapeutic peptides and proteins: Technology landscape of lipid-based nanocarriers; Advanced Drug Delivery Reviews, vol. 182, 114097, Jan. 7, 2022.

IOI Oleochemical, Miglyol® 812 N & Imwitor® 742 Product Spotlights, 2025, https://www.ioioleo.de/wp-content/uploads/IO1_Spotlights_Pharma_WEB.pdf (accessed Jul. 29, 2025), 2025.

* cited by examiner

*Primary Examiner* — Bethany P Barham
*Assistant Examiner* — Judith Marie Kamm
(74) *Attorney, Agent, or Firm* — Blank Rome

(57) ABSTRACT

A method of treating type-2 diabetes, chronic weight maintenance, or overindulgence conditions includes administering a pharmaceutically effective amount of a topical composition comprising a GLP-1 receptor agonist suspended in an anhydrous suspension base vehicle to an oral cavity of a subject for oral absorption therein. The topical composition is formulated to form a self-emulsifying liposome in an aqueous environment of the oral cavity.

15 Claims, No Drawings

TOPICAL ADMINISTRATION OF GLP-1 RECEPTOR AGONISTS

TECHNOLOGY

The present disclosure relates to compositions and methods of making and using GLP-1 receptor agonists for topical administration.

BACKGROUND

Glucagon-like peptide-1 (GLP-1) receptor is a transmembrane receptor involved in mediation of intracellular signaling pathways that regulate glucose metabolism, insulin production and secretion, glucagon secretion, gastric emptying, appetited satiation, among others. GLP-1 hormone is a ligand of the GPL-1 receptor and is released in the gastrointestinal tract by "L" cells in response to nutrient consumption. Activation of the GLP-1 receptor upon ligand binding stimulates insulin secretion and slows glucagon secretion, which reduces blood glucose. Activation also slows stomach emptying and interacts with appetite control mechanisms in the brain to signal satiation. GLP-1 receptor agonists are subcutaneously injected daily or weekly to mimic GLP-1 hormone for weight-loss or treat type-2 diabetes. The GLP-1 receptor agonist semaglutide is available in a tablet format for oral administration to the gastrointestinal tract.

SUMMARY

In one aspect, a topical composition for administration to an oral cavity for oral absorption therein to treat type-2 diabetes, chronic weight maintenance, or overindulgence conditions includes a pharamecutically effective amount of semaglutide suspended in an anhydrous suspension base vehicle. The topical composition for oral absorption may further includes phosphatidylcholine, lysophosphatidylcholine, polycarbophil, glyceryl distearate, glyceryl monostearate, magnesium stearate, microcrystalline cellulose, povidone, and salcaprozate sodium.

In one example, the topical composition for oral absorption may further include caprylic/capric triglyceride.

In the above or another example, the topical composition for oral absorption may further include sucralose, *Siraitia grosvenorii* (monk) fruit, marshmallow oil flavor, or combination thereof.

In another aspect, a method of treating type-2 diabetes, chronic weight maintenance, or overindulgence conditions includes administering to an oral cavity of a subject for oral absorption therein a pharmaceutically effective amount of semaglutide suspended in an anhydrous suspension base vehicle. The topical composition further includes phosphatidylcholine, lysophosphatidylcholine, polycarbophil, glyceryl distearate, and glyceryl monostearate.

In one example, the topical composition further comprises sucralose, *Siraitia grosvenorii* (monk) fruit, or both. The topical composition may further include marshmallow oil flavor.

In the above or another example, the topical composition further includes magnesium stearate, microcrystalline cellulose, povidone, and salcaprozate sodium.

In any of the above or another example, the topical composition further includes caprylic/capric triglyceride.

In any of the above or another example, the topical composition further includes glyceryl monostearate, glyceryl distearate, or both.

In yet another aspect, a method of formulating a topical composition for topical administration to the oral cavity for oral absorption therein to treat type-2 diabetes, chronic weight maintenance, or overindulgence conditions includes combining semaglutide powder with an anhydrous suspension base vehicle to formulate a suspension. The suspension is formulated to form a self-emulsify liposome in an aqueous environment of the oral cavity.

In one example, the suspension includes phosphatidylcholine and lysophosphatidylcholine, In the above or another example, the suspension further includes polycarbophil.

In a further example, the suspension includes glyceryl distearate and glyceryl monostearate.

In any of the above or another example, the suspension further includes caprylic/capric triglyceride.

In any of the above or another example, the suspension further includes sucralose, *Siraitia grosvenorii* (monk) fruit, or both.

In any of the above or another example, the suspension further includes marshmallow oil flavor.

In one example, the suspension further includes magnesium stearate, microcrystalline cellulose, povidone, salcaprozate sodium, polycarbophil, glyceryl distearate, glyceryl monostearate, phosphatidylcholine, lysophosphatidylcholine, caprylic/capric triglyceride, sucralose, *Siraitia grosvenorii* (monk) fruit, or combination thereof.

In one aspect, a method of treating type-2 diabetes, chronic weight maintenance, or overindulgence conditions includes administering a pharmaceutically effective amount of a topical composition comprising semaglutide suspended in an anhydrous suspension base vehicle to an oral cavity of a subject for oral absorption therein. The semaglutide may be encapsulated within liposomes suspended in the anhydrous suspension base vehicle.

In one example, the topical composition further includes a flavorant.

In another aspect, a method of formulating a topical composition for topical administration to the oral cavity for oral absorption includes combining semaglutide powder with an anhydrous suspension base vehicle to formulate a suspension. The anhydrous suspension base vehicle may include a liposomal or mixed micelle system or the method may further include combining preliposomes to formulate a liposomal or mixed micelle system. The preliposome system may include phospholipids.

In one example, the combining further includes combining a flavorant.

In still another aspect, a method of formulating a topical composition for topical administration to the oral cavity for oral absorption includes combining semaglutide with a base vehicle to formulate a suspension.

In one example, the suspension is an anhydrous suspension. A flavorant may be embedded in the anhydrous suspension base vehicle.

In one example, the combining further includes a flavorant.

In one example, the semaglutide is combined with the base vehicle in a powder format. The powder format may further include preliposomes. The powder format may further include a flavorant.

In one example, the base vehicle includes a liposomal or mixed micelle system.

In one example, the topical composition is a composition for sublingual or buccal administration.

In yet another aspect, a method of formulating a topical composition for topical administration to external skin or mucosa of a vagina, rectum, oral cavity, or nasal cavity of a subject for transdermal or transmucosal delivery there along. The method may further include combining semaglutide with a base vehicle to formulate a suspension.

In one example, the suspension is an anhydrous suspension.

In one example, the semaglutide is combined with the base vehicle in a powder format. The powder format may further include preliposomes.

In one example, the base vehicle includes a liposomal or mixed micelle system.

In one example, the base vehicle includes a cream, ointment, solution, lotion, suspension, gel, paste, or foam.

In still yet another aspect, a method of treating type-2 diabetes, chronic weight maintenance, or overindulgence conditions includes administering a pharmaceutically effective amount of a topical composition comprising a GLP-1 receptor agonist and a base vehicle to external skin or mucosa of a vagina, rectum, oral cavity, or nasal cavity of a subject for transdermal or transmucosal delivery there along.

In one example, the base vehicle includes a cream, ointment, solution, lotion, suspension, gel, paste, or foam.

In one example, the GLP-1 receptor agonist is encapsulated or otherwise associated with liposomes or prelip_somes suspended in the base vehicle. The base vehicle may be an anhydrous suspension base vehicle.

In one example, the topical composition is formulated to self-emulsify in an aqueous environment to for a self-emulsifying liposome.

In one example, the topical composition further comprises a flavorant.

In another aspect, a method of treating a type-2 diabetes, chronic weight maintenance, or overindulgence condition comprises administering a pharmaceutically effective amount of a topical composition comprising semaglutide suspended in an anhydrous suspension vehicle to an oral cavity of a subject for oral absorption therein.

In one example, the semaglutide is obtained or originates from ground commercial oral tablet containing semaglutide.

In one example, the oral tablet comprise RYBELSUS® tablets.

In still yet another aspect, a method of formulating a topical composition for topical administration to the oral cavity for oral absorption includes combining powder of a crushed commercial GLP-1 receptor agonist oral tablet with a vehicle to formulate a suspension.

In one example, the GLP-1 receptor agonist is sema_glutide.

DESCRIPTION

The present disclosure describes various embodiments of a composition for topical administration comprising a GLP-1 receptor agonist and methods of making and using the same. In some embodiments, the GLP-1 receptor agonist may comprise or consist of semaglutide. Additionally or alternatively, the GLP-1 receptor agonist may comprise or consist of liraglutide, exenatide, lixisenatide, taspoglutide, lotiglipron, dulaglutide, tirzepatide, albiglutide, danuglip_ron, orforglipron, efpeglenatide, or combination thereof.

In various embodiments, the topical composition may be formulated for topical administration via transmucosal or transdermal routes. For example, the topical composition may be formulated for topical administration to an external skin or mucosal surface. In some examples, the topical composition may be formulated for topical administration to mucosa lining at a natural body orifice, such as the oral cavity, nasal cavity, vagina, or rectum. In one embodiment, the topical composition comprises an anhydrous suspension formulated to form a self-emulsifying liposome in an aqueous environment.

As introduced above, the topical composition may be formulated for topical administration to mucosal tissue for transmucosal delivery. For example, the topical composition may be topically administered to the oral cavity for oral absorption therein. As a further example, the topical composition may be administered to the oral cavity for oral absorption sublingually, buccally, or otherwise.

When GLP-1 receptor agonists are administered via the oral route to the digestive system, plasma albumin binding may be in excess of 99%. Topical administration, e.g., transmucosal via oral absorption, substantially lowers dosing required to achieve a same or similar impact compared to the oral route by nullifying or minimizing the impact of plasma albumin binding and 1st pass metabolism. Thus, the topical compositions and methods for topical administration described herein may beneficially avoid plasma albumin binding and effects of 1st pass metabolism. This break-through will reduce dosing requirements and associated patient costs without limiting efficacy. The topical compositions and methods for topical administration described herein may also be used to benefit patients in a manner similar to injectables but without the hassle, pain, and costs of dealing with injectables.

In various embodiments, the topical composition may be used to treat type-2-diabetes or weight loss. In some embodiments, the topical composition may also be used to treat behaviors associated with overindulgence, such as binge behaviors and/or compulsions. Example conditions include those related to binge eating, drinking, or shopping; excessive or compulsive use of social media, electronic devices, television, drugs, tobacco, nicotine, shoplifting; or sex addiction, to name a few. In one example, the topical composition may be used to treat alcoholism.

In various embodiments, the topical composition comprises a GLP-1 receptor agonist in a base vehicle for topical oral absorption within the oral cavity. The GLP-1 receptor agonist may be selected from semaglutide, liraglutide, exenatide, lixisenatide, taspoglutide, lotiglipron, dulaglutide, tirzepatide, albiglutide, danuglipron, orforglipron, efpeglenatide, or combination thereof. A composition formulated for oral absorption may comprise a solution, semisolid, or solid format. The topical composition may comprise a powder, solution, suspension, gel, paste, tablet, or lozenge format for transmucosal delivery via oral absorption. The topical composition may be a dry powder, aqueous, a colloidal suspension (e.g., an emulsion), anhydrous, or as otherwise formulated. For example, the topical composition may be provided in an aqueous solution or anhydrous solution base vehicle. The topical composition may be provided in colloid format, such as an emulsion or other suspension format. The topical composition may be provided in a gel format. The topical composition may be provided in a solid format.

The topical composition may be compounded into various oral absorption formats. For example, in one embodiment, the topical composition may be a solution or suspension for application under the tongue or within the buccal pouch by a syringe or dropper. In one example, the topical composition comprises a mouthwash or rinse for transmucosal delivery via the mouth. In some embodiments, the topical composition may be formulated for oral absorption to include flavoring to improve patient compliance due to its ease of use and enhanced taste. In one embodiment, the topical composition comprises a suspension including a GLP-1 receptor agonis in a base vehicle for topical oral absorption. The suspension may be absorbed in the mouth, e.g., sublingually, buccally, or otherwise. In one example, the suspension is an anhydrous suspension. The suspension may include phospholipids to create an innovative system that delivers the active ingredients directly to the mucous membranes under the tongue and/or buccal pouch. The phospholipids may include lipid aggregates comprising liposomes, micelles, or both.

In various embodiments, the topical composition comprises semaglutide encapsulated by, associated with, or in the presence of a liposomal or mixed micelle system during administration. The system may be a mixed micelle system including liposomes or liposome free. The system may include substantially pure liposomes such that the system includes aggregate lipids that are mainly or substantially associated in bilayers. All or a portion of the GLP-1 receptor agonist may be encapsulated by or associated with liposomes, micelles or both. In one example, the GLP-1 receptor agonist may not necessarily be encapsulated in liposomes and/or micelles and may be within the topical composition in the presence of lipids such as phospholipids, which may include liposomes and/or mixed micelles. The topical composition may be aqueous, a colloidal suspension (e.g., an emulsion), anhydrous, or as otherwise formulated. In one example, the topical composition comprises a lipid based, preliposomal, or mixed micelle system in an anhydrous suspension base vehicle. The anhydrous suspension base vehicle may ensure the stability and potency of the liposomes or mixed micelle for optimal performance when activated in an aqueous environment. In further embodiments, the liposomal or mixed micelle system in an anhydrous suspension base vehicle. The anhydrous suspension base vehicle may ensure the stability and potency of the liposomes for optimal performance. In some examples, the GLP-1 receptor agonist, such as semaglutide, is solubilized in the anhydrous suspension. The topical composition may have surprising stability. For example, the topical composition may be stable for 90 days or longer. In various embodiments, the topical composition is anhydrous. In further embodiments, the liposomal or mixed micelle system may be utilized in compositions for transmucosal or transdermal delivery at other body surfaces, e.g., external skin, nasal cavity, vaginal, or rectal. In one embodiment, the topical composition includes polycarbophil to prolong contact. The topical composition may be anhydrous and activate upon interaction with an aqueous environment self-emulsify to form a liposomal or mixed micelle system. In an embodiment for oral absorption, the topical composition employs film-forming adhesion ingredients that create a protective film to minimize initial contact of the active agent drug with tastebuds.

The topical composition may be provided at any suitable dosage of GLP-1 receptor agonist, which may be determined by those skilled in the art in view of the present disclosure. In various applications, choice of dosage may consider one or more of the conditions treated, severity, patient profile, dosing frequency, format, or route of delivery. Satiation treatment for weight loss, for instance, may benefit from larger doses than doses for diabetes. Overindulgence treatment may benefit from larger doses than satiation. Patients with greater body mass may benefit from larger doses than those with less body mass. Transdermal delivery may benefit from larger doses than transmucosal delivery. Various dosing schedule may be used. For example, dosing may be once or twice a day or as otherwise prescribed. Dosing may be weekly or twice weekly in some applications. Larger dosages may be found appropriate in less frequent dosing regimens.

In various embodiments, the topical composition is administered in an active dose between 0.01 mg to 100 mg for oral absorption or other transmucosal or transdermal route. For example, the topical composition may be administered in a dose between about 1 mg and about 30 mg, between about 20 mg and about 40 mg, between about 30 mg and about 50 mg, between about 40 mg and about 60 mg, between about 50 mg and about 100 mg, between about 80 mg and about 100 mg, between about 60 mg and about 100 mg, between about 10 mg and about 40 mg, between about 20 mg and about 60 mg, between about 30 mg and about 70 mg, between about 40 mg and about 80 mg, between about 50 mg and about 90 mg, between about 60 mg and about 100 mg, between about 70 mg and about 100 mg, greater than 10 mg, greater than 25 mg, greater than 50 mg, or greater than 75 mg. In one example, the above dosing is once or twice a day, split between multiple doses a day, every other day, twice weekly, or as otherwise determined suitable.

In one embodiment, the topical composition may be administered to the mouth for oral absorption or other transmucosal delivery route in an active dose amount between about 0.1 mg and about 1 mg, between about 0.1 mg and about 0.8 mg, between about 0.1 mg and about 0.6 mg, between about 0.1 mg and about 0.6 mg, between about 0.25 mg and about 0.5 mg, or between about 0.5 mg and about 1 mg. In some embodiments, dosing with respect to some GLP-1 receptor agonists, such as exenatide or lixisenatide, may be less than 0.01 mg. For example, dosing may be between about 0.001 mg and 0.01 mg, such as between about 0.003 mg and about 0.01 mg, between about 0.005 mg and about 0.01 mg. Such dosing may be beneficial in daily or twice daily dosing via transmucosal delivery. Larger dosing may be determined to be appropriate for transmucosal or transdermal delivery. For example, the topical composition may be administered in a dose between about 1 mg and 20 mg, such as between 1 mg and about 5 mg, between about 1 mg and about 10 mg, between about 1 mg and about 15 mg, between about 2 mg and about 6 mg, between about 3 mg and about 10 mg, between about 4 mg and about 15 mg, between about 6 mg and about 15 mg, between about 10 mg and about 20 mg, between about 10 mg and about 15 mg, or between about 15 mg and about 20 mg.

The topical composition may be provided at any suitable concentration. Appropriate concentrations may be determined by those skilled in the art in view of the present disclosure. In various applications, choice of concentration may consider the desired dosage, administration volume/weight, route of delivery, or other consideration. For example, higher concentrations may be reasonable for lower administration volumes. In one example, concentration of GLP-1 receptor agonist, such as semaglutide, in the topical composition may be between about 0.001% and about 10% (w/v). For example, the topical composition formulated for transmucosal delivery may be provided at a concentration between about 0.001% and about 0.01%, between about 0.001% and about 0.1%, about 0.05% and about 1%, between about 0.05% and about 0.5%, between about 0.08% and about 0.2%, between about 0.08% and about 0.15%, between about 0.075% and about 0.125%, between about 0.01% and about 0.1%, between about 0.1% and about 1%, between about 1% and about 2%, between about 2% and about 5%, between about 4% and about 8%, greater than 0.08%, less than 0.5%, less than 0.3%, or less than 1.5%. Greater or lesser concentrations may also be used. Compositions for transdermal delivery may be provided at concentrations similar to those listed above with respect to transmucosal. In one embodiment, the topical composition comprises suspension provided at about 0.5 mg/mL, about 1 mg/mL, about 1.5 mg/mL, about 2 mg/mL, about 2.5 mg/mL, about 3 mg/mL, about 4 mg/mL, about 6 mg/mL, about 10 mg/mL, about 50 mg/mL, or about 100 mg/mL.

In one formulation, the topical composition may comprise a dry powder format. The powder may be loose, encapsulated, or compressed in a tablet form for administration to the mouth, e.g., a buccal or sublingual tablet. The powder may be placed under the tongue, along the gums and/or cheeks (e.g., within the buccal pouch) to dissolve, wet, hydrate, solubilize, or reconstitute all or a portion of the powder contents with saliva in situ for transmucosal absorption. For example, in a preliposome format, the powder may reconstitute in situ for liposome formation and delivery by oral absorption. In one embodiment, the powder may be provided in a pouch for administration to the mouth. In one embodiment, the powder is provided within a capsule including a liquid separated from the powder. The capsule may be mechanically broken down or dissolved in biological fluid to combine the powder and liquid in situ. In various embodiments, the topical composition comprises a powder base vehicle. In these or other embodiments, the topical composition comprises one or more surfactants, pH adjusting agents, flavorants, viscosity modifiers, preservatives, or the like.

In various embodiments, the powder may comprise or consist of particle sizes from very fine to micronized, such as less than about 50 microns, less than about 40 microns, less than about 30 microns, less than about 25 microns, or less than about 20 microns. In some examples, the particle sizes represent an average or a majority of the particles within the range, such as at least 50%, at least 60%, at least 70%, at least 80%, at least 90%, at least 95%, or at least 98%. In a further example, the remaining particles outside the particle range may be no more than about 25%, about 20%, about 15%, about 10%, or about 5% larger.

As described in more detail below, in some embodiments, compositions in a powder format may be topically administered to skin, mucosa, or both. In further embodiments, the topical composition may be compounded from a powder or powder mixture that is mixed with a base vehicle. The base vehicle may comprise a solution (e.g., aqueous, anhydrous), colloidal suspension (e.g., emulsion, anhydrous suspension), oil, ointment, cream, lotion, paste, gel, or other suitable base vehicle for topical administration.

The topical composition comprising a powder for administration in a powder format or a powder for mixing with a non-powder base vehicle, may include one or more additional ingredients, such as xylitol, poloxamers, salcaprozate sodium, sodium caprate, lactose, starch, magnesium stearate, cellulose or cellulose derivatives, microcrystalline cellulose, sugar, sugar alcohol, povidone, talc, or combination thereof. In embodiments comprising or formulated for combination with a liquid or semi-liquid base vehicle, the powder, base vehicle, or otherwise the topical composition may include one or more additional ingredients, such as xylitol, poloxamers, salcaprozate sodium, sodium caprate, lactose, starch, magnesium stearate, cellulose or cellulose derivatives, microcrystalline cellulose, sugar, sugar alcohol, povidone, talc, or combination thereof. In some embodiments, additional ingredients in the topical composition may include a sodium glucose cotransporter 2 inhibitor. For example, a sodium glucose cotransporter 2 inhibitor may be selected from one or more of canagliflozin, dapagliflozin, empagliflozin or ertugliflozin.

As introduced above, in some embodiments, the topical composition comprises a liposomal or mixed micelle delivery system. In one example, the topical composition comprises a powder mixture of preliposomes and semaglutide. In a further example, the preliposomal powder mixture may include one or more additional ingredients, such as xylitol, poloxamers, salcaprozate sodium, sodium caprate, lactose, starch, magnesium stearate, cellulose or cellulose derivatives, microcrystalline cellulose, sugar, sugar alcohol, povidone, talc, or combination thereof. The preliposomal powder may include or be mixed with GLP-1 receptor powder or liquid. The preliposomal powder may be reconstituted prior to administration. For example, the preliposomal powder may be formulated for reconstitution with a liquid medium to compound a solution or suspension. The liquid medium may comprise, for example, an aqueous medium, anhydrous medium, emulsion, oil, water, or other suitable medium for topical administration to the mouth or other desired body surface. In one example, the preliposomal powder may include or be mixed with GLP-1 receptor powder or liquid. The mixture may be further mixed with an anhydrous medium prior to administration, which may be minutes, hours, days, or months prior to administration.

In some embodiments, the preliposomal powder may be formulated for reconstitution in situ. For example, the topical composition powder may be administered to a skin or mucosal surface, such as the mouth, for reconstitution upon interaction with body fluids. For instance, the topical composition may comprise a powder for administration to the nasal cavity. Administration may deposit the topical composition along nasal mucosal of the nares. Administration may deposit the topical composition along mucosa of the sinus. In one example, the topical composition comprises preliposomes configured for liposomal delivery upon reconstitution with body fluid as described herein. As introduced above, powder formats may include tablets, capsules, or loose powder. In one example, the preliposome powder may be dispersed within an oral lozenge medium, buccal tablet, sublingual tablet, or contained within a pouch for oral absorption upon reconstitution in situ. In some embodiments, the powder or base vehicle medium may include one or more flavorants and/or sweeteners described herein. In some embodiments, the topical composition comprising a preliposome powder may be mixed with a base vehicle to compound a suspension, cream, lotion, ointment, gel, or paste for topical administration via transmucosal or transdermal delivery.

In various embodiments, the topical composition may be provided in a liquid format. The liquid format may comprise an anhydrous lipid suspension comprising GLP-1 receptor agonist suspending in a lipid vehicle including phospholipids. Such suspensions may comprise liposomal or mixed micelle systems. In one example, liposomal or mixed micelle systems are referred to as preliposomes formulated to form liposomal or mixed micelle systems upon the addition of aqueous liquid or when placed within an aqueous environment. In a further example, the preliposomes and base vehicle comprise self-emulsifying liposomes upon addition of aqueous liquid or when placed within an aqueous environment.

In one embodiment, the topical composition comprises a suspension. The suspension may be administered to the mouth for oral absorption. In one example, the suspension may be compounded just before administration by combining ingredients of the topical composition with a liquid base vehicle, which may include one or more components thereof, and mixing to compound the suspension. In another example, the suspension may be compounded days, weeks, or months before administration. Thus, the suspension may be stable over extended periods of time. In one example, the suspension comprises an anhydrous base vehicle. The base vehicle may comprise an oil, which may include an oil mixture. The base vehicle may comprise a lipid-based drug delivery system. In one formulation, the base vehicle comprises an emulsion. The base vehicle may be a buffered suspending base vehicle, syrup, elixir, or the like. The suspension may include various additional ingredients such as surfactants, penetrant enhancers, chelates, pH adjusting agents, flavorants and/or sweeteners, viscosity modifiers, preservatives, release agent (e.g., sustained, controlled, delayed, or extended), absorption modifiers, or the like. In one example, the one or more additional ingredients comprise xylitol, poloxamers, salcaprozate sodium, sodium caprate, lactose, starch, magnesium stearate, cellulose or cellulose derivatives, microcrystalline cellulose, sugar, sugar alcohol, povidone, talc, or combination thereof. In one example, the topical composition does not include preservatives. In one embodiment, the topical composition comprises semaglutide suspended in an anhydrous base vehicle including lipids in a preliposome formulation. In various embodiments, the topical composition comprises one or more permeation enhancers to boost delivery into and through buccal or gingival tissue. In one example, the topical composition or the base vehicle comprises diethylene glycol monoethyl ether NF.

As introduced above, in various embodiments, the topical composition comprises a liposomal or mixed micelle system. For example, the topical composition may include a liposomal base vehicle suspension encapsulating or associating GLP-1 receptor agonist, such as semaglutide. In a further example, liposomes may encapsulate or otherwise associate with GLP-1 receptor agonist and one or more additional ingredients. The topical composition may comprise mixed micelles. The mixed micelles may encapsulate or otherwise associate with the GLP-1 receptor agonist. The one or more additional ingredients may comprise xylitol, poloxamers, salcaprozate sodium, sodium caprate, lactose, starch, magnesium stearate, cellulose or cellulose derivatives, microcrystalline cellulose, sugar, sugar alcohol, povidone, talc, or combination thereof. In a further or another example, one or more additional ingredients may be within the liposome containing medium, which may be in addition to or instead of being encapsulated within the liposomal delivery base vehicle. For example, xylitol, poloxamers, or both may be within the liposome containing medium and GLP-1 receptor agonist may be encapsulated alone or together with one or more additional ingredients selected from salcaprozate sodium, sodium caprate, lactose, starch, magnesium stearate, cellulose or cellulose derivatives, microcrystalline cellulose, sugar, sugar alcohol, povidone, talc, or combination thereof. In some embodiments, additional ingredients may include a sodium glucose cotransporter 2 inhibitor, such as one selected from one or more of canagliflozin, dapagliflozin, empagliflozin or ertugliflozin.

In various embodiments, the liposomal or mixed micelle system comprises liposomes and/or micelles within an anhydrous medium, which may be preliposomal or otherwise lipid based prior to initiation upon aqueous exposure. In another example, the base vehicle comprises liposomes and/or micelles within an emulsion. In one example, the topical composition comprises an anhydrous liposomal or micelle base vehicle suspension encapsulating, associating, or in the presence of semaglutide. In some embodiments, the suspension is compounded by mixing a preliposomal powder, semaglutide, and a liquid base vehicle, which may be just prior to administration or earlier. In one embodiment, a liposomal or mixed micelle system comprises an anhydrous liquid base vehicle, e.g., comprising lipids such as phospholipids, oils, or both. The anhydrous liquid base vehicle may have a preliposomal format configured to self-emulsify as described here. In other formulations, a liquid base vehicle comprises an aqueous base vehicle. In some embodiments, the suspension is compounded by mixing the base vehicle with GLP-1 receptor agonists, such as semaglutide. The base vehicle may comprise an anhydrous liquid including phospholipids. The base vehicle may be configured to self-emulsify in an aqueous environment, which may be an in situ environment driven by aqueous biological fluid or aqueous liquid added to or supplemented to an administration site or added prior to administration to the administration site.

The topical composition comprising a liposomal or mixed micelle system may be formulated for oral absorption, e.g., sublingually, buccally, or otherwise. The topical composition comprising a liposomal or mixed micelle system may be formulated for transmucosal delivery rectally, nasally, or vaginally. The topical composition comprising a liposomal or mixed micelle system may be formulated for transdermal delivery to an exterior skin surface. In some embodiments, the topical composition comprising a liposomal or mixed micelle system comprises a suspension, ointment, cream, lotion, gel, paste, or solution.

In various embodiments, the topical composition includes one or more permeation enhancing ingredients. Permeation enhancing ingredients may be provided within a vehicle or added a vehicle described here. Permeation enhancing ingredients may be included to boost delivery into and through buccal or gingival tissue. Example, permeation enhancing ingredients may include diethylene glycol monoethyl ether NF (Transcutol HP). In some embodiments, permeation enhancing ingredients are selected that also have emulsifying or surfactant action to impart a self-emulsifying aspect to the topical composition. Permeation enhancing ingredients may be included in compositions comprising liposomal or mixed micelle systems.

In various embodiments, the topical composition configured for oral absorption includes one or more flavorants and/or sweeteners. For example, flavorants and/or sweeteners may be provided in a powder composition format (loose powder, pouch, tablet, capsule, or otherwise), suspension composition format, a solution composition format, a lozenge composition format, or other format for oral absorption. The flavorant may be natural, artificial, synthetic, or combination thereof. Sweeteners may comprise one or more of artificial, synthetic, or natural sweeteners. In one example, sweeteners include *Siraitia grosvenorii* (monk) fruit. In this or another example, sweeteners include sucralose. The flavorant may include methyl salicylate, one or more natural essential oils, or combination thereof. The flavorant may include a natural or artificial oil. Oils may include lemon, peppermint, lavender, or rose, as examples. The flavorant may comprise or be obtained from a flavored powder such as banana, chocolate, strawberry, vanilla, pineapple, mango, or other suitable flavored powder. Example flavorants may include bitter taste flavorants such as chocolate, peanut oil, olive oil, walnut, almond, wild cherry, sesame oil, corn oil, mint, anise, monk fruit, marshmallow oil, or combination thereof. Flavorants may include cherry, grape, raspberry, peppermint, cinnamon, peach, orange, mixed fruit, apricot, honey, butterscotch, clove, ginger, ethyl maltol, cardamon, capric acid, malic acid, ethyl acetate, methionine, maltol, spearmint, menthol, or combination thereof.

In various embodiments, the topical composition formulated for oral absorption may be mixed with water or an aqueous solution such as juice prior to the time of administration. For example, a powder, aqueous suspension, colloidal suspension, or anhydrous suspension as described above and elsewhere herein may be mixed with water or an aqueous solution such as juice prior to administration, which may be immediately prior, e.g., within an hour, or longer for stable formulations. In one example, the topical composition comprising a self-emulsifying anhydrous base vehicle may be configured to be mixed with an aqueous liquid prior to administration. The self-emulsifying anhydrous base may comprise an anhydrous liquid or powder. The self-emulsifying anhydrous base may comprise a lipid based delivery system. The self-emulsifying anhydrous base may comprise a liposomal and/or mixed micelle system formulated to form self-emulsifying liposomes when in an aqueous environment or upon addition of an aqueous liquid.

As introduced above, the topical composition may be formulated for transmucosal and/or transdermal delivery via application to external skin or mucosa of the oral cavity, nasal cavity, vagina, or rectum. In various embodiments, the topical composition is provided in a format selected from a colloid or emulsion (o/w, w/o), cream, lotion, ointment, foam, aqueous or non-aqueous gel, aqueous or non-aqueous solution or suspension, anhydrous suspension, dispersion, paste, or powder. Powder formats include those described above and elsewhere herein, including loose powder, buccal tablet, sublingual tablet, capsule, pouch, lozenge, as well as suppository. As also introduced above, various embodiments of the topical composition may be compounded by combining a powder including the GLP-1 receptor agonist with a base vehicle to compound compositions having a desired format. Additional ingredients, such as those described herein, may also be present in the powder, base vehicle, or mixed therewith.

The base vehicle may be liquid, semi-liquid, or solid. For example, the base vehicle may include an aqueous, anhydrous, organic, or inorganic solution, which may include a dispersion or suspension, cream, gel, ointment, lotion, emulsion, powder, or paste. In some embodiments, the base vehicle includes a base cream, ointment, gel, lotion, foam, or solution. The base vehicle may include base vehicle components such as lecithin, phospholipids, glycols, paraffin, fatty acids, carbopols/carbomers, alcohols, lanolin, for example.

In some embodiments, the base vehicle comprises an aqueous solution. In some examples, base vehicles comprising an aqueous solution may be combined with ingredients of the topical composition to formulate the same. In an embodiment, the base vehicle or component thereof may include an aqueous solution comprising a saline solution. For example, the topical composition may comprise a base vehicle or component comprising a sodium hydroxide solution, which may be a sterile solution, an alcohol, water, e.g., purified water, water for irrigation, water for injection, or a sterile water. In one embodiment, a base vehicle or component thereof comprises a sodium chloride 0.09% solution (sterile). The base vehicle or component may be present in an amount sufficient to obtain the desired amount of active agents per unit weight or volume.

In some embodiments, the topical composition may include a base vehicle comprising a polyethylene glycol (PEG) base vehicle component. In other embodiments, the topical composition is PEG-free. In these or other embodiments, the topical composition may include a silicon or silicon variant base vehicle component. In some embodiments, the topical composition is silicon-free. An example composition may comprise a solution including base vehicle components selected from water, alcohol, DMSO, saline or sodium chloride, sodium hypochlorite, or other aqueous or anhydrous base vehicle medium into which the one or more of the topical composition ingredients are mixed, dispersed, suspended, solubilized, or dissolved. The topical composition may be water soluble/miscible or formulated for water absorption. The topical composition may comprise a water-in-oil emulsion or oil-in-water emulsion. In one embodiment, the topical composition comprises a emulsion, e.g., a cream or lotion format, comprising one or more base vehicle components selected from of acrylate copolymer, alcohol, camphor, carbomer, dimethyl isosorbide, disodium EDTA, dl-alphatocopheryl acetate, edetate disodium, emulsifying wax, eucalyptus oil, flavonoids, glycerin, glycol dicaprylate/dicaprate, hydroxyethyl cellulose, isopropyl myristate, lactic acid, meadowsweet extract, menthol, mineral oil, neopentyl, phenolic glycosides, polyethylene glycol (PEG), polysorbate (e.g., polysorbate 85, polysorbate 20), purified water, titanium dioxide, tridecyl stearate, tridecyl trimellitate, sodium hydroxide, sodium hydroxide, sorbitol, stearic acid, zinc pyrithione, or combinations thereof. In some embodiments, the topical composition comprises a foam format that includes a propellant base vehicle component such as butane. Compositions comprising a foam format may also comprise additional characteristics such as that of an emulsion, such as an oil-in-water emulsion, or gel.

In one example, the topical composition comprises an ointment format comprising base vehicle components selected from hydrophilic petrolatum, white petrolatum, hydrophilic ointment, white ointment, anhydrous lanolin, hydrous lanolin, PEG ointment, or combinations thereof. In an embodiment, the topical composition comprises a gel format. The gel may be an aqueous or anhydrous gel. The gel may include base vehicle components including thickening agents and/or gelling agents such as carbopol, poloxamer, xanthan gum, methylcellulose, carboxymethyl cellulose, hydroxyethyl cellulose, ethylcellulose, gelatin, magnesium aluminum silicate, polyvinyl alcohol, sodium alginate, or combinations thereof.

The topical composition or base vehicle thereof may include base vehicle components such as one or more solubilizers, stabilizers, buffers, tonicity modifiers, bulking agents, viscosity enhancers/reducers, surfactants, chelating agents, adjuvants, or combinations thereof.

In various embodiments, the topical composition or base vehicle thereof comprises one or more glucose polymers such as a starch, cellulose or cellulose derivatives, polydextrose, or combination thereof. Example starches may include sodium starch glycolate, corn starch, pregelatinized starch, or combination thereof. Example celluloses may include hydroxypropyl cellulose, hypermellose, croscarmellose sodium, ethyl cellulose, microcrystalline cellulose, or combination thereof. Povidone such as povidone K30, copovidone, crospovidone, or combination thereof, may also be present. In some embodiments, glycol and/or a sugar alcohol may be present. Example glycols may include polyethylene glycol, propylene glycol, or combination thereof. Example sugar alcohols may include mannitol. Some embodiments may include oxides such as silicon dioxide, titanium dioxide, ferric oxide, or combination thereof. One embodiment may include any of the above and magnesium stearate, talc, diethyl phthalate, sodium stearyl fumarate, sodium lauryl sulfate, polysorbate, triacetin, polacrilin, lactose, glycerol behenate, polyvinyl alcohol, carnauba wax, or combination thereof. In one embodiment, the topical composition does not include one or more of starch, cellulose, polydextrose, sodium starch glycolate, corn starch, pregelatinized starch, hydroxypropyl cellulose, hypermellose, croscarmellose sodium, ethyl cellulose, microcrystalline cellulose, povidone, povidone K30, copovidone, crospovidone, polyethylene glycol, propylene glycol, mannitol, silicon dioxide, titanium dioxide, ferric oxide, magnesium stearate, talc, diethyl phthalate, sodium stearyl fumarate, sodium lauryl sulfate, polysorbate, triacetin, polacrilin, lactose, glycerol behenate, polyvinyl alcohol, carnauba wax, or combination thereof.

In some embodiments, the base vehicle comprises a water washable, moisturizing ointment comprising polyethylene glycol, water, Spiraea ulmaria flower extract, zinc acetate, and propylene glycol. In one embodiment, the polyethylene glycol comprises PEG-8 and PEG-75.

In various embodiments, the topical composition is anhydrous and comprises GLP-1 receptor agonist in an anhydrous base vehicle. In one example, the GLP-1 receptor agonist is semaglutide. The topical composition may be formulated for self-emulsification in aqueous environments. For example, the topical composition may include ingredients that impart self-emulsification to the topical composition in aqueous environments. In some embodiments, the aqueous environment is an administration site and the topical composition self-emulsifies in situ. The aqueous environment may be provided by biological fluids. In instance, administration to the mouth may expose the topical composition to saliva, thereby driving self-emulsification. In some embodiments, self-emulsification drives liposome and/or mixed micelle formation for transmucosal or transdermal administration.

In some embodiments, the topical composition comprises medium chain triglycerides NF, glycerin USP, glyceryl distearate NF, stearoyl polyoxyl-32 glycerides NF, ascorbyl palmitate NF, vitamin E acetate USP, and *Siraitia grosvenorii* (monk) fruit extract and GLP-1 receptor agonist. In one example, the GLP-1 receptor agonist is semaglutide. For example, an anhydrous self-emulsifying base vehicle may comprise medium chain triglycerides NF, glycerin USP, glyceryl distearate NF, stearoyl polyoxyl-32 glyerides NF, ascorbyl palmitate NF, vitamin E acetate USP. A flavorant and/or sweetener, such as those described herein, may be included or added to the topical composition. The topical composition may further include a nonionic water-dispersible surfactant for lipid-based formulations to solubilize and enhance the oral bioavailability of poorly water-soluble APIs. The topical composition may self-emulsify in aqueous media, forming a fine dispersion, which may be referred to as a microemulsion (SMEDDS).

In one example, the topical composition may be formulated in a base vehicle configured to spontaneously form a self-emulsifying liposome, which may include micelle or mixed micelles, for improved drug delivery. For instance, the topical composition may comprise a self-emulsifying liposome formulation designed to form an emulsion upon contact with aqueous fluids, e.g., saliva in a sublingual administration. The topical composition may be anhydrous and self-emulsify in aqueous environments. The topical composition may be formulated to self-emulsify in situ. For instance, administering the topical composition to the oral cavity of a subject may cause the topical composition to self-emulsify when interacting with saliva. This process may occur without addition of mechanical or thermal energy. In various embodiments, the anhydrous self-emulsifying base vehicle comprises a self-emulsifying liposome base vehicle comprising phosphatidylcholine and lysophosphatidylcholine. For example, the base vehicle may include a synergistic combination of about 0.5% w/w to about 10% w/w of phosphatidyl-choline, preferably about 3% w/w, and about 0.1% w/w to about 1% w/w of lysophosphatidylcholine, preferably about 0.36% w/w.

In some embodiments, the base vehicle comprises an anhydrous lipid based vehicle configured for self-emulsification in an aqueous environment. In one example, the base vehicle may comprise caprylic/capric triglyceride. In this or another example, the base vehicle comprises a glyceryl stearate, such as a monostearate, distearate, or both. In either example or another example, the base vehicle comprises phosphatidylcholine, lysophosphatidylcholine, polycarbophil, glyceryl distearate, and glyceryl monostearate. In any of the above or another example, the base vehicle may include a flavorant, e.g., a flavor and/or sweetener, as described herein, such as monk fruit, natural oil flavor, sucralose, or combination thereof. Formulation of the topical composition may comprise combining powder including the GLP-1 receptor agonist and the base vehicle. The base vehicle may be preformulated prior to combining or one or more ingredients may be further combined. For instance, one or more flavorants or sweeteners may be added before or after combining powder with other components of the base vehicle.

In various embodiments, the topical composition incorporates polycarbophil. Polycarbophil may enhance the topical composition to achieve both prolonged contact time and effective bitterness masking. The prolonged contact time and effective bitterness masking may position the topical composition as a prime choice for sublingual drug delivery.

Additionally or alternatively, the topical composition may incorporate a specialized technology designed to counteract the bitterness often associated with drugs like semaglutide. For example, the topical composition may employ a unique film-forming adhesion technology that combines glyceryl distearate, glyceryl monostearate, and polycarbophil. The combination works synergistically to create a protective film that minimizes the drug's initial and direct contact with the taste buds, thereby reducing bitterness. Optionally, sweeteners and/or flavors may be added to further diminish any residual bitter taste during ingestion. Example sweeteners and flavors may include those identified herein, such as marshmallow oil flavor, sucralose, *Siraitia grosvenorii* (Monk) fruit, or combination thereof.

In one embodiment, the topical composition utilizes synergistic properties of glyceryl distearate, glyceryl monostearate, and polycarbophil. For instance, when applied sublingually, these ingredients collaboratively form a protective matrix. This matrix firmly adheres to the sublingual mucosa, thereby prolonging the formulation's contact with the mucosal surface. The extended contact time, primarily facilitated by polycarbophil, enhances the absorption of active ingredients through the sublingual route, leading to increased bioavailability and optimized therapeutic efficacy. Concurrently, glyceryl distearate and glyceryl monostearate form an anhydrous film that not only improves drug contact time but also minimizes the drug's interaction with taste buds, reducing bitterness. The combination of polycarbophil, glyceryl distearate, and glyceryl monostearate also acts as an effective bitterness-mitigating agent, skillfully masking the bitter taste of certain active ingredients.

Table 1 provides an example base vehicle for combination with GLP-1 receptor agonist to generate a self-emulsifying suspension. The suspension may be anhydrous and be configured to self-emulsify within an aqueous environment, e.g., in situ, which may be provided by biological fluid at the administration site. The base vehicle in Table 1 is also formulated for taste masking and adhesion as introduced above.

TABLE 1

| Anhydrous Suspension Vehicle | | | | |
| --- | --- | --- | --- | --- |
| Material Name | INCI | % Material | % Range | Exemplary |
| GELEOL MONO AND DIGLYCERIDES NF | GLYCERYL MONOSTEARATE | 2 | 0.5-5 | 2 |
| PRECIROL ATO5 | GLYCERYL DISTEARATE | 1 | 0.5-5 | 1 |
| GELUCIRE 48/16 | PEG-32 STEARATE | 3 | 1-5 | 3 |
| LABRAFIL M1944 | APRICOT KERNEL OIL PEG-6 ESTERS | 1.5 | 0.2-5 | 1.5 |
| PUREFRUIT SELECT | SIRAITIA GROSVENORII FRUIT EXTRACT | 1.3 | 0.5-2 | 1.3 |
| SUCRALOSE | SUCRALOSE | 1 | 0.0-2 | 1 |
| CAPRYLIC/CAPRIC TRIGLYCERIDES | CAPRYLIC/CAPRIC TRIGLYCERIDE | 80.6 | 60-95 | 80.4 |
| PHOSAL 53 MCT | LECITHIN CAPRYLIC/CAPRIC TRIGLYCERIDE ALCOHOL GLYCERYL STEARATE OLEIC ACID ASCORBYL PALMITATE TOCOPHEROL | 6 | 1-10 | 6 |
| NOVEON AA-1 POLYCARBOPHIL | POLYCARBOPHIL USP | 0.6 | 0.2-2 | 0.6 |
| MARSHMALLOW O.S NAT | NATURAL FLAVOR | 3 | 1-5 | 3 |
| | | (SUM) 100 | | |

The ingredient PHOSAL 53 MCT contains a minimum of 53% of phosphatidylcholine and a maximum of 6% lyso-phosphatidylcholine. In some embodiments, the base vehicle includes a synergistic combination of about 0.5% w/w to about 10% w/w of phosphatidylcholine and about 0.1% w/w to about 1% w/w of lysophosphatidylcholine. A current preferred formulation includes about 3% w/w phosphatidylcholine and about 0.36% w/w lysophosphatidylcholine. As described above and elsewhere herein flavorant may be optional and may be added separately. One or more ingredients may also be excluded or replaced by pharmaceutical ingredients determined to be equivalent.

Table 2 illustrates an example compounding procedure to formulate a topical composition comprising a semaglutide suspension. As shown, the base vehicle comprises a self-emulsifying liposome suspension (Table 1), however, other base vehicles described herein may also be used. The procedure includes mixing ground commercial oral semaglutide tablets (RYBELSSU® 14 mg) and base vehicle (Table 1). The tablets were ground separately. Ingredients were weighted using an appropriate balance. The ingredients where combined in an electronic mortar and pestle container and mixed once on normal in an Ungator 2100. The viscosity preferably ranges from 100 to 1500 CPS and while depend on inclusion or exclusion of wetting agents and oil flavors.

TABLE 2

| Semaglutide Suspension Formula | |
| --- | --- |
| Semaglutide tablet, ground | Q.S. |
| Base Self-emulsifying liposome suspension | Q.S. |
| Wetting agent (optional) | 2 to 10%, preferred 5% |
| Flavor (optional) | 0.2-3%, preferred 1% |

A method of making the topical composition may comprise mixing powder including the GLP-1 receptor agonist with vehicle, which may be referred to as a base vehicle. The base vehicle may be anhydrous in a liquid state including lipids. The base vehicle may be an anhydrous base vehicle in a liquid state including phosphatidylcholine and lyso-phosphatidylcholine. The base vehicle may additionally or alternatively include polycarbophil. The base vehicle may additionally or alternatively include glyceryl distearate and glyceryl monostearate. The base vehicle may be self-emulsifying as described herein. The base vehicle may comprise a base vehicle as described in Table 1 or elsewhere herein. To prepare the topical composition, the user may triturate the powder. The powder may optionally be wetted with a wetting agent. Example wetting agents include propylene glycol or glycerin. Upon adding the base vehicle and mixing, the topical composition's solubility in the lipid suspension is enhanced. When applied sublingually, it spontaneously forms a self-emulsifying liposome, improving drug delivery. For even more refined preliposome formation, an electric mortar and pestle may be utilized. This tool can offer a more consistent and thorough mixing, ensuring the highest quality of the end product.

In various embodiments, the topical composition may be administered topically by contacting an external surface of the body, which may include skin or a vaginal or anal orifice, for absorption there along. The topical composition may be administered to the oral cavity or nasal cavity for absorption therein. The topical composition may be administered in a spray, coat, soak, powder, spread, or the like, for example, suitable to the topical format.

A method of compounding the topical composition may include obtaining all or a portion of the GLP-1 receptor agonist alone or together with one or more additional ingredients from a powder format, e.g., from bulk powder, crushed tablet, injection powder, or other commercially available composition. The powder may be mixed with a base vehicle, such as those described herein. The method may include combining the base vehicle and a powder containing all or a portion of the GLP-1 receptor agonist. For example, the GLP-1 receptor agonist may be obtained from commercial tablets, crushed and/or ground to a desired particle size. In one embodiment, all or a portion of the GLP-1 receptor agonist may be obtained from a commercially manufacture injection powder or solution and mixed with the base vehicle to compound the topical composition. In one example, GLP-1 receptor powder is wetted prior to combining with the base vehicle. For instance, according to various compounding methods, the powder may be wetted with DMSO, alcohol, or water. In one embodiment, the powder may be wetted with propylene glycol or glycerin. According to a method, all or a portion of additional ingredients may be provided in a format selected from a solution, emulsion, gel, cream, lotion, ointment, or other format and may be combined with the base vehicle together with or separate of all or a portion of the GLP-1 receptor agonist. In one example, all or a portion of additional ingredients may be mixed with all or a portion of the GLP-1 receptor agonist prior to being mixed with other ingredients of the base vehicle. In another example, the GLP-1 receptor agonist is added to additional ingredients that are provided in a commercially available medicated composition comprising the base vehicle. The base vehicle may comprise a commercially available base vehicle including one or more additional ingredients and a powder or other format including the GLP-1 receptor agonist may be mixed therewith to compound the topical composition. For instance, a suspending base vehicle including a flavorant may be mixed with GLP-1 receptor agonist for administration to the oral cavity via oral absorption. In one example, the GLP-1 receptor agonist is obtained from ground commercial oral tablets for oral administration. The powder may be mixed with a base vehicle comprising phospholipids and/or preliposomes for subsequent reconstitution with liquid base vehicle components. The powder may be mixed with a phospholipid base vehicle to formulate a liposomal or mixed micelle system. In one example, the powder is mixed with a suspension base vehicle including a liposomal or mixed micelle system. In one formulation the base vehicle is an anhydrous liquid. The base vehicle may be anhydrous in a liquid state including lipids. The base vehicle may be an anhydrous base vehicle in a liquid state including phosphatidylcholine and lysophosphatidylcholine. The base vehicle may additionally or alternatively include polycarbophil, glyceryl distearate, and glyceryl monostearate. The base vehicle may be self-emulsifying as described herein. In a further example, the base vehicle optionally includes a flavorant or a flavorant is added. The base vehicle may comprise a base vehicle as described in Table 1 or elsewhere herein.

In some embodiments, the topical composition comprising an anhydrous self-emulsifying composition may be combined with aqueous liquid prior to administration to drive emulsification. In one embodiment, the emulsification may generate a microemulsion. In one embodiment, the emulsification generates a liposomal or mixed micelle system.

The number of tablets used to prepare the GLP-1 receptor agonist for compounding to compound the topical composition comprising a desired weight of GLP-1 receptor agonist may be determined by dividing the weight of GLP-1 receptor agonist needed by the weight of GLP-1 receptor agonist in a tablet. The weight of tablet powder needed to formulate a composition comprising a desired weight of GLP-1 receptor agonist may be determined by dividing the weight of a tablet by the weight of GLP-1 receptor agonist present in the tablet and multiplying the result by the desired weight of GLP-1 receptor agonist in the topical composition.

In one embodiment, a method of compounding the topical composition includes crushing or obtaining powder from crushed oral commercial tablets of a GLP-1 receptor agonist. In one example, the topical composition is formulated from commercial oral semaglutide tablets. Tablets may be ground, preferably separately from the vehicle. Any desired strength formulations may be formulated according to the present description. For instance, an oral tablet may be weighed to determine the amount of semaglutide per measurement unit. This formula may then be used to determine the amount of tablet powder needed for combination with vehicle and any additional ingredients to obtain the desired percent composition. For example, a 14 mg RYBELSUS® tablet has an average weight of 0.409 gm. To formulate a semaglutide 1 mg/ml composition using powder from the 14 mg semaglutide oral tablet, each ml of the topical composition includes 1 mg of semaglutide, which is $\frac{1}{14}$ or 7.14% of one tablet. Thus, each ml of the topical composition includes 29.214 mg of tablet powder and the desired concentration may be obtained by mixing the powder with vehicle and any other ingredients to the volume corresponding to the weight of tablet powder for the desired concentration. The appropriate amount of powder including the desired amount of semaglutide may be mixed with the desired base vehicle. The base vehicle may be any base vehicle described herein. For example, the base vehicle may be an aqueous, non-aqueous, anhydrous, emulsion, liquid, semi-solid, or solid base vehicle. Mixing the base vehicle and crushed semaglutide tablet powder may formulate a power, solution, suspension, ointment, cream, gel, or paste. In one embodiment, a resulting powder may be compressed into a tablet format or encased in a capsule or pouch for administration to the mouth via buccal, sublingual, or other oral absorption delivery. In one embodiment, the mixture may be fully or partially solidified to generate a gel or oral absorption lozenge. In one embodiment, the base vehicle comprises an anhydrous suspension base vehicle. In a further embodiment, the base vehicle comprises an anhydrous suspension base vehicle including liposomes. As described herein the liposomes may be within a mixed micelle system or may be provided pure such that the system includes aggregate lipids that are mainly or substantially associated in bilayers. In one embodiment, the vehicle comprises a mixed micelle system free of liposomes. In one example formulation the suspension base vehicle is formulated to self-emulsify in an aqueous environment. In one embodiment, the base vehicle comprises an anhydrous suspension base vehicle and is mixed with a powder comprising the crushed semaglutide tablets and preliposomes. In one embodiment, the anhydrous suspension or powder includes mixed micelles, with or without preliposomes. The base vehicle, powders, or mixture may include or be combined with additional ingredients, such as those described herein. In one example, the additional ingredients include a flavorant and/or sweetener. For example, the flavorant may include a sweetener to mask the bitter taste of semaglutide, other GLP-1 receptor agonist, or other active agent. In one embodiment, the flavorant and/or sweetener may be added to the crushed tablet powder. For example, compounding the topical composition may include triturating the flavorant, e.g., sweetener powder, with the crushed tablet powder and then mix with the base vehicle, which may be an anhydrous. In one embodiment, the flavorant may be embedded in the base vehicle. For example, the flavorant, e.g., sweetener powder, may be embedded in the base vehicle and compounding the topical composition includes combining the crushed tablet powder with the base vehicle. In some embodiments, the flavorant may be provided as a liquid. In one example, the flavorant may be used to wet the crushed tablet powder.

The present disclosure describes various embodiments of compositions including semaglutide. However, it is to be understood that such embodiments may additionally or alternatively include other GLP-1 receptor agonists, such as liraglutide, exenatide, lixisenatide, taspoglutide, lotiglipron, dulaglutide, tirzepatide, albiglutide, danuglipron, orforglipron, efpeglenatide, or combination thereof. Thus, all the various embodiments including semaglutide are additionally or alternatively disclosed as including one or more GLP-1 receptor agonists. The GLP-1 receptor agonists may include independently or in combination one or more of semaglutide, liraglutide, exenatide, lixisenatide, taspoglutide, lotiglipron, dulaglutide, tirzepatide, albiglutide, danuglipron, orforglipron, efpeglenatide, or other GLP-1 receptor agonist. The chemical compounds, active agents, and other ingredients described herein are to be understood as encompassing derivatives, analogs, and pharmaceutically acceptable equivalents unless indicated otherwise. Base vehicles described herein may refer to the excipient portion of a topical composition and does not necessarily refer to a set of ingredients that are combined prior to addition of an active agent. Indeed, ingredients of a base vehicle may be combined with the base vehicle (other ingredients) in whatever order is suitable for formulation of the topical composition. For example, when included, flavorants and/or sweeteners may be combined with actives, other base vehicle ingredients, or combinations thereof independently or in combinations in any order that achieves the flavorant and/or sweetener function together with the functions of the topical composition.

Embodiments described herein that include self-emulsifying base vehicles or that are otherwise formulated to self-emulsify in an aqueous environments may be topically administered as described herein. For example, the topical composition may be administered for transdermal or transmucosal delivery. The topical composition may be administered to the oral cavity, anus, rectum, nasal cavity, ear, or vagina.

The topical composition comprising the anhydrous self-emulsifying base vehicle, while beneficial for sublingual administration, is versatile and can be utilized for other areas due to its self-emulsifying liposome feature. Thus, beyond administration to the oral cavity, the topical composition it adaptable for administration in nasal, oral, vaginal, topical, and even hair care formulations. Given its multifunctional design, it offers a broad spectrum of possibilities in drug delivery and care solutions, even those beyond delivery of GLP-1 receptor agonists. Indeed, those having skill in the art will appreciate upon reading the present description that embodiments described herein including self-emulsifying base vehicles or that are otherwise formulated to self-emulsify in an aqueous environment may include one or more active agents in addition to or instead of one or more GLP-1 receptor agonists. Example non-limiting actives may be selected from analgesics, androgenic hormones, antacids, antianxiety drugs, antiarrhythmics, antibacterials, antibiotics, anticoagulants, antidepressants, antidiarrheals, antiemetics, antifungals, antihistamines, antihypertensives, anti-inflammator antineoplastics, antipsychotics, antipyretics, antivirals, anxiolytics, barbiturates, beta-blockers, bronchodilators, cold medicines, corticosteroids, cough suppressants, cytotoxics, decongestants, diuretics, expectorant, hormones, hypoglycemics, immunosuppressives, laxatives, mucolytics, muscle relaxants, sedatives, sleeping aids, thrombolytics, tranquilizer, or vitamins. Such topical compositions may be administered to treat conditions such active agents are used to treat in the art. Such topical compositions may be topically administered as described herein for transdermal or transmucosal delivery. For example, the topical compositions may be administered to the oral cavity, anus, rectum, nasal cavity, ear, or vagina. The topical composition may be administered to external skin surfaces.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular preferred arrangements disclosed for carrying out this invention, but that the invention will include all embodiments and arrangements falling within the scope of the appended claims.

Various elements described herein have been described as alternatives or alternative combinations, e.g., in a list of selectable actives, ingredients, or compositions. It is to be appreciated that embodiments may include one, more, or all of any such elements. Thus, this description includes embodiments of all such elements independently and embodiments including such elements in all combinations. Any component or ingredient disclosed herein may be explicitly excluded in an embodiment. In various embodiments, the topical composition may be free of biologics, nucleic acids, corn, soy, monosaccharides, disaccharides, milk, collagen, nuts, fish, shellfish, penicillin, hydrocarbons, alcohol, NSAIDs, anticonvulsants, gluten, or combination thereof. In one example, the topical composition is free of sulfonamides, which may be in addition to being free of one or more of the above.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a range is stated as 1 to 50, it is intended that values such as 2 to 40, 10 to 30, 1 to 3, or 2, 25, 39 and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" or "about" are intended to include +/−10% of the number modified.

What is claimed is:

1. A method of treating type-2 diabetes, chronic weight maintenance, or overindulgence conditions, the method comprising:

administering a topical composition to an oral cavity of a subject for oral absorption therein, the topical composition comprising a pharmaceutically effective amount of semaglutide suspended in an anhydrous liquid comprising phosphatidylcholine, lysophosphatidylcholine, caprylic/capric triglyceride, polycarbophil, glyceryl distearate, and glyceryl monostearate, wherein the topical composition is self-emulsifying and forms mixed micelles and liposomes associated with the semaglutide in an aqueous environment of the oral cavity.

2. The method of claim 1, wherein the topical composition further comprises sucralose, *Siraitia grosvenorii*, or both.

3. The method of claim 2, wherein the topical composition further comprises marshmallow oil flavor.

4. The method of claim 1, wherein the topical composition further comprises magnesium stearate, microcrystalline cellulose, povidone, and salcaprozate sodium.

5. The method of claim 4, wherein the topical composition further comprises sucralose, *Siraitia grosvenorii*, or both.

6. The method of claim 2, wherein the oral absorption is sublingual.

7. The method of claim 2, wherein the oral absorption is buccal.

8. The method of claim 5, wherein the topical composition further comprises marshmallow oil flavor.

9. The method of claim 4, wherein the oral absorption is buccal.

10. The method of claim 4, wherein the oral absorption is sublingual.

11. The method of claim 1, wherein the topical composition further comprises marshmallow oil flavor.

12. The method of claim 1, wherein the oral absorption is sublingual.

13. The method of claim 1, wherein the oral absorption is buccal.

14. The method of claim 9, wherein the topical composition further comprises sucralose, *Siraitia grosvenorii*, and marshmallow oil flavor.

15. The method of claim 10, wherein the topical composition further comprises sucralose, *Siraitia grosvenorii*, or both.

* * * * *